April 18, 1972 J. M. GARABEDIAN Plant Pat. 3,124
GRAPEVINE
Filed April 29, 1970
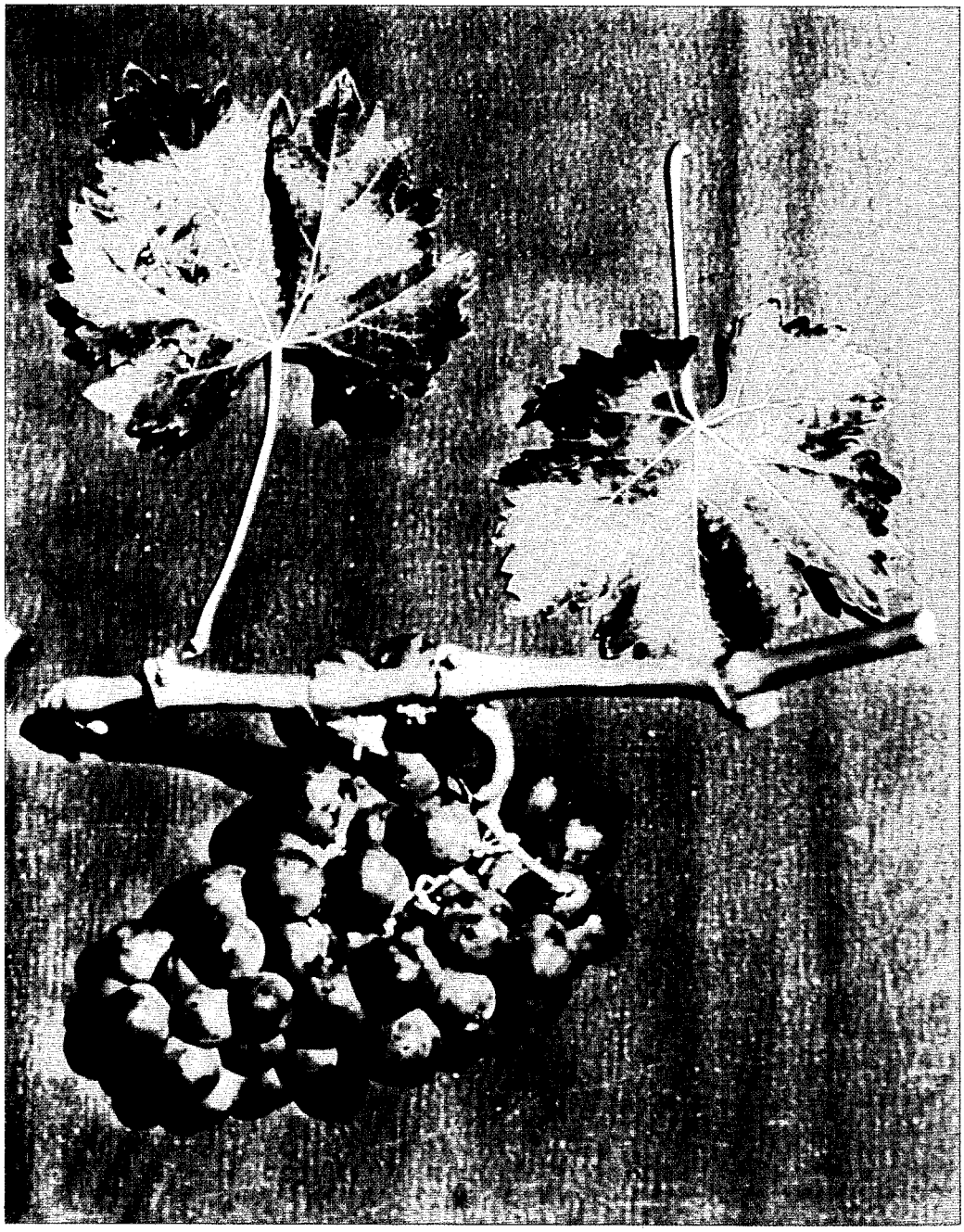
INVENTOR
John M. Garabedian
BY
Webster & Webster
ATTORNEYS

United States Patent Office

Plant Pat. 3,124

Patented Apr. 18, 1972

3,124

GRAPEVINE

John M. Garabedian, 3158 Hamilton St., Fresno, Calif. 93712

Filed Apr. 29, 1970, Ser. No. 33,110

Int. Cl. A01h *5/03*

U.S. Cl. Plt.—47 1 Claim

ABSTRACT OF THE DISCLOSURE

A large to medium size, vigorous grapevine, having mostly long canes, which is a regular and productive bearer of red table grapes—of superior eating quality—borne in usually conical, large to medium size clusters wherein the individual berries are usually large; the berries, which are mostly ellipsoidal, ripen about one week earlier than the Cardinal (unpatented), have firmer, more meaty flesh, less watery juice, a vinous to neutral flavor, a sweet taste attributable to a higher sugar content, and seeds which are smaller.

ORIGIN OF THE VARIETY

The present variety of grapevine was originated by me, on a ranch of which I am an owner, located near Madera, Madera County, Calif., as a cross between the Cardinal and an unnamed seedless sport (unpatened) previously found by me in a vineyard (of which I am also an owner) located near Fresno, Fresno County, Calif. The seedling vine, which resulted from the above described cross, was maintained by me under careful and continuing observation, and—upon the vine bearing fruit—I recognized its new and distinctive characteristics and which classed it as a superior table grape. The variety was, therefore, selected for asexual reproduction preparatory to ultimate vineyard planting thereof.

ASEXUAL REPRODUCTION OF THE VARIETY

Subsequent to origination of the present variety of grapevine, and recognition of its advantageous characteristics, I asexually reproduced such variety by budding onto mature grapevines in a vineyard on the aforesaid ranch located near Madera, Madera County, Calif. When grown to maturity, and in bearing, such asexual reproductions ran true to the original grapevine in all respects.

SUMMARY OF THE VARIETY

The herein claimed variety of grapevine, in comparison to the Cardinal and as to which there is general resemblance, is new and distinct, essentially, in that the vine, which is large to medium in size, is more vigorous with mostly long canes, and is a regular and productive bearer of red table grapes of superior eating quality. More particularly, the grapes are borne in usually conical, large to medium size clusters wherein the individual berries—which are usually large, mostly ellipsoidal in form, and ripen about one week earlier—have firmer, more meaty flesh, less watery juice, a vinous to neutral flavor, and a sweet taste attributable to a higher sugar content.

The herein claimed variety of grapevine, in further comparison to the Cardinal, has pyriform seeds which are smaller and of which a substantially greater number are non-viable as is desirable in a table grape, a beak which is narrower and longer, a hilum usually smaller, and a small to medium, oval, chalaza located mostly below the center of the seed body.

BRIEF DESCRIPTION OF THE DRAWING

The drawing is an illustration, by photographic reproduction in color, of leaves, a length of cane, and a cluster of berries of the variety.

DESCRIPTION OF THE VARIETY

The botanical details of this new and distinct variety of grapevine—with color definitions (except those in common color terms) referenced to Maerz and Paul Dictionary of Color—are as follows:

Vine:

*Size.*—Large to medium.
*Vigor.*—Strong.
*Growth.*—Vigorous to medium.
*Productive Capacity.*—Good.
*Trunk.*—Long, slender.
*Bark.*—Ribbons, long fibers, strap much fissured.
*Bark Texture.*—Brittle.
*Color of bark.*—Top bark—much darker than light tan of Cardinal. Under bark—medium brown.
*Canes.*—Dimensions (current season's growth)—2½′ to 12½′. Length—long to medium—mostly long (longest cane on specimen vine—19′). Form (cross section) — circular to slightly flattened. Thickness—medium; width at node—7/16″; width at internode—5/16″ (variable). Color—current season's growth—light green (21-L-5); one-year old growth—top bark—striated Blue Haze grey (38-A-3)—under bark—Rosedust brown (6-B-2).
*Shoots.*—Glabrous.
*Nodes.*—Average distance between nodes—3½″ to 5¾″ (variable). Length—medium. Form—prominent.
*Tendrils.*—Length—long, average length—4½″ to 9½″. Form—simple to mostly trifurcated—few quadfurcated. Thickness—medium, average thickness—3/32″. Texture—smooth. Location—discontinuous—mostly intermittent. Number per cane—6 to 9. Color—parrot green (21-L-6).

Foliage:

*Density.*—Heavy to medium.
*Leaves.*—Outline—dentate.
*Blade.*—Size—mostly large. Thickness—thick to medium. Dimensions—medium, average length—5¼″; average width—8⅛″.
*Contour.*—Plane, smooth.
*Petiole.*—shallow; medium to wide; U-shaped; base rounded. Texture—tough; brittle. Length—long—average 145 mm. Thickness—thick—average 2.5 mm. Color—Dorsal—Sea green (19-K-6), with reddish overcolor on one-half near leaf of blade. Ventral—Rainette green (21-K-4).
*Texture.*—Thick; leathery; brittle.
*Color.*—Dorsal—Dark green (24-L-8). Ventral—Lighter green (23-L-7).
*Lobes.*—Number—mostly 5.
*Leaf vein.*—Midrib color—Grape green (21-I-1).
Margin.—Teeth—6–8 points per lobe; usually large blunt tooth at apex of each lobe; pointed to blunt; serrate to dentate; medium length; medium angle; margin series mostly 2–3.
*Pubescence.*—Glabrous to very little pubescence.
*Number of tendrils.*—6–9 per cane.
*Time leaves fall.*—Somewhat earlier than Cardinal.

Buds:

*Shape.*—Conical.
*Size.*—Average length—5 mm. Average width—5 mm.
*Position.*—Angle of about 50° to 60°.
*Pubescence.*—Pubescent.

Inflorescences:

Number borne per cane 1–4.—Number borne per vine 40–45.

Flowers:

*Size of peduncle.*—Medium; average length—2⅛"; average width—3/16".

*Node where fruit produced.*—From 1st to 5th node—mostly on nodes 3 and 4.

*Type of flower.*—Fertile.

Bloom.—Date of first bloom—May 10, 1969. Date of full bloom—May 17, 1969. Date of last bloom—May 20, 1868.

Pedicel.—Adherence to berry—strong. Smoothness.—Smooth. Length—mostly long; some medium; average—8.6 mm.

*Pistil.*—Color—Green. Length at pollination—2 cm. Glands at base of pistil.—Present.

*Stamens.*—Number—6. Filaments—Straight. Length of filaments—Medium, average 1.5 mm. Amount of pollen—Abundant.

Fruit:

*Ripening period.*—Early—about one week ahead of Cardinal. Date of first picking—July 15, 1968. Date of last picking—July 25, 1968.

*Cluster dimensions.*—Average length—9⅛"; average width—5 7/16".

*Stem color.*—Grape green (21-L-5).

Main truck stem (Rachis).—Length—Medium. Thickness—Medium.

*Secondary branches.*—Number—few. Length—short. Texture—Brittle.

*Cluster form.*—Mostly conical—some cylindrical; intermediate length; many adhering shoulders.

*Cluster size.*—Large to medium.

*Number of clusters per cane.*—Average—2.

*Cluster weight.*—Average—15.4 ounces.

Cluster compactness.—Well filled; loose.

*Cluster location.*—Mostly at 4th and 5th nodes—some at 6th node.

*Berries.*—Size—mostly large. Uniformity of berry size.—mostly uniform. Dimensions.—Longitudinal axis—average 24.4 mm. diameter axis—average 23.3 mm. Berry set—Good. Number of berries per cluster—average—96. Form—mostly ellipsoidal; many spherical. Skin—medium thick; tough. Taste—sweet.

*Color.*—Port Wine red (56-J-12).

*Lenticels.*—1 at apex on most berries.

*Berry bloom.*—Moderate; Grayish.

*Pulp.*—Adheres to skin; greenish white color.

*Berry texture.*—Firm; Crisp.

*Berry color under skin.*—Greenish opaque, some reddish speckling.

*Tendency to crack.*—None.

*Color of juice.*—Whitish opaque green to clear.

*Juice.*—Very sweet to sweet.

*Juice solids.*—Sugar (Balling Saccharimeter Test Averages). July 13, 1968—17.3%; September 13, 1968—26% (Cardinal on same date—18%); November 21, 1968—30.9% (Cardinal on same date—19.45%).

*Flavor.*—Vinous to neutral.

*Taste.*—Sweet.

*Capstem.*—Length—mostly long; some medium; average 8.6 mm. Thickness—Medium; average 2 mm. Adherence—strong. Torus—medium size; mostly rough and glandular. Brush—medium length—average 7.2 mm. Light green color. Color of capstem—fern green (20-K-8).

*Seeds.*—Amount—Few to many; average 260 seeds per 100 berries. Size—mostly medium; average length—7.8 mm.; average width—4.1 mm. Weight—average per 100 seeds—5.6 grams. Seed form—pyriform. Body form—mostly cuneate; some oblong. Beak—Straight; medium length; sharp. Keel—mostly flattened; some sharp to rounded. Suture—dorsal—not prominent, narrow, shallow. Ventral—prominent, narrow, shallow. Hilum—Small. Color (immature)—Grape green (21-K-1). Color (mature)—Brown. Chalaza—Small to medium; Mostly below center; Oval; Sunken slightly; Most have high ridge margin. Texture—Crisp. Taste—Sharp; Bitey. Non-viable seeds—average—67 per 100 seeds.

*Fruiting habit.*—On main canes—Some clusters at 2nd–3rd nodes, but mostly at 4th–6th nodes.

*On lateral canes.*—Clusters at 6th–7th nodes.

Use: Dessert.

Keeping quality: Good.

The present variety resulted from the same cross as the variety of grapevine disclosed in copending plant patent application Ser. No. 33,111.

The grapevine and its fruit herein described may vary in slight detail due to climatic and soil conditions under which the variety may be grown; the present description being of the variety as grown in the Central Valley of California.

I claim:

1. A new and distinct variety of grapevine, substantially as illustrated and described, which is characterized, in comparison to the Cardinal, by a large to medium size vine which is more vigorous with mostly long canes, a regular and productive bearer of red table grapes borne in usually conical, large to medium size clusters wherein the individual berries—which are usually large, mostly ellipsoidal, and ripen about one week earlier—have smaller seeds, firmer more meaty flesh, less watery juice, a vinous to neutral flavor, and a sweet taste attributable to a higher sugar content.

No references cited.

ROBERT E. BAGWILL, Primary Examiner